US005776871A

United States Patent [19]
Cothran et al.

[11] Patent Number: 5,776,871
[45] Date of Patent: Jul. 7, 1998

[54] SHAMPOOS WITH INSOLUBLE SILICONE CONDITIONING AGENT AND CATIONIC POLYMER

[75] Inventors: Philip Earl Cothran, Loveland; Thomas Francis Gauthier, Milford; Timothy Woodrow Coffindaffer, Loveland, all of Ohio

[73] Assignee: The Procter & Gamble Company, Cincinnati, Ohio

[21] Appl. No.: 852,935

[22] Filed: May 8, 1997

Related U.S. Application Data

[63] Continuation of Ser. No. 428,923, Apr. 21, 1995, abandoned.
[51] Int. Cl.$^6$ ........................................ C11D 1/82
[52] U.S. Cl. ................ 510/122; 510/119; 510/125; 514/881
[58] Field of Search ........................ 510/119, 122, 510/125; 514/852, 880, 881; 424/59, 70

[56] References Cited

U.S. PATENT DOCUMENTS

| 4,983,383 | 1/1991 | Maksimoski et al. | 424/70 |
| 5,160,730 | 11/1992 | Dubief et al. | 424/59 |

FOREIGN PATENT DOCUMENTS

| 432951 | 6/1991 | European Pat. Off. | A61K 7/075 |
| 0468721 | 1/1992 | European Pat. Off. | |
| 674898 | 10/1995 | European Pat. Off. | A61K 7/075 |
| 91/15947 | 10/1991 | WIPO | A01J 21/00 |
| 94/03152 | 2/1994 | WIPO | A61K 7/50 |
| 04/06403 | 3/1994 | WIPO | A61K 7/06 |
| 94/06409 | 3/1994 | WIPO | A61K 7/50 |

*Primary Examiner*—Glenn Caldarola
*Assistant Examiner*—Alexander G. Ghyka
*Attorney, Agent, or Firm*—Darryl C. Little; Tara M. Rosnell; Jacobus C. Rasser

[57] ABSTRACT

Provided is a anti-dandruff shampoo composition comprising: (a) from about 8% to about 40%, by weight, of detersive surfactant, said composition comprising from about 5% to about 40% of anionic detersive surfactant; (b) from about 0.05% to about 5%, by weight, of a dispersed, insoluble silicone conditioning agent; (c) from about 0.01% to about 1.0%, by weight, of a stabilizing agent for the silicone conditioning agent, said stabilizing agent being a shampoo soluble cationic polymer; (d) from about 50% to about 91.5%, by weight, water; wherein said shampoo composition is substantially free of suspending agents selected from the group consisting of crystalline suspending agents and anionic, nonionic, and amphoteric polymeric thickening agents.

19 Claims, No Drawings

SHAMPOOS WITH INSOLUBLE SILICONE CONDITIONING AGENT AND CATIONIC POLYMER

This is a continuation of application Ser. No. 08/428,923, filed on Apr. 21, 1995, now abandoned.

TECHNICAL FIELD

The present invention relates to shampoo compositions containing an insoluble silicone conditioning agent. In particular, the present invention relates to shampoo compositions containing an insoluble silicone conditioning agent stably suspended with a low level of cationic polymer.

BACKGROUND OF THE INVENTION

Shampoo compositions which both cleanse the hair and condition the hair with insoluble silicone conditioning agents are well known. Among the preferred types of insoluble silicone conditioning agents are nonvolatile polydimethyl siloxanes, which are typically dispersed in the shampoo as an emulsion, wherein the silicone is present as a dispersed phase of droplets in the aqueous shampoo formula. In order for these types of shampoos to be effective and to provide a consistent level of performance, without requiring vigorous shaking of the package in which they are contained, it is conventional practice to suspend them in the composition with the aid of a suspending agent. Since shampoos are likely to remain on shelves or in storage for long periods of time, it is important for the suspending agents to keep the insoluble conditioning agent well suspended for relatively long periods of time. The suspending agents which have become preferred for suspension of insoluble silicone conditioning agents are those which form a crystalline network in the shampoo when the shampoo is stationary, but which allow the composition to readily flow when shear is applied, such as when a user pours it out of a bottle. Examples of such crystalline suspending agents include ethylene glycol distearate and N, N-di-(hydrogenated tallow) amido benzoic acid.

Another drawback of crystalline suspending agent is that they require costly heating and cooling steps in the manufacture of the compositions in order to make high quality stable suspensions.

Yet another important parameter in the formulation of shampoos is lathering. The consuming public often associates high lathering with effective cleaning, and typically prefers high lathering shampoos to low lathering shampoos from an aesthetic standpoint. Unfortunately, crystalline suspending agents tend to adversely affect lathering performance.

Other suspending agents which are known include hydrophilic polymeric thickening agents such as cellulosic gums and crosslinked acrylic acid/acrylate polymers, the latter of which are commonly referred to as carbomers. Although these materials can be effective for suspending insoluble silicone they can impart an undesirable, slimy feel.

It is well known in the art to add foaming agents to help compensate for lather reductions caused by suspending agents. Examples of such foaming agents include cocomono-and di-ethanol amide, betaine surfactants, soluble long chain alcohols such as $C_{12}$–$C_{14}$ monohydric alcohols, amine oxides, and cationic polymers such as cationic modified xanthan gum and hydroxy-ethyl cellulose. However, the addition of these ingredients does not overcome the other disadvantages of conventional suspending agents, adds further cost to the shampoo, and may also increase harshness of the shampoo.

It would be desirable to provide liquid shampoo composition with a stable dispersed insoluble silicone conditioning agent, which also did not require the use of conventional suspending agents such as crystalline suspending agents or polymeric thickening agents to suspend the silicone.

It is therefore an object of this invention to provide shampoos containing insoluble silicone conditioning agents that are suspended without the need for crystalline suspending agents.

It is yet another object of this invention to provide shampoos containing insoluble silicone conditioning agents that are suspended without the need for conventional, hydrophilic polymeric thickening agents.

It is still another object of this invention to provide compositions, as set forth above, which can be made without the need for costly heating and cooling steps, as conventionally utilized when crystalline suspending agents are employed.

It is yet another object of this invention to provide a process for making conditioning shampoos meeting the above objects. These and other benefits as may be apparent or otherwise realized can be obtained according to the present invention, which is described below. Unless otherwise indicated, all percentages are calculated by weight of the total composition, and all ratios are calculated on a weight basis. Unless otherwise indicated, ingredients are based on the active level and therefore do not include carriers or by-products that may be included in commercially available materials. The present invention may comprise, consist of, or consist essentially of any of the essential and various optional and/or preferred ingredients and elements described herein. The terms "soluble" and "insoluble" shall refer to the solubility characteristics of a particular ingredient in the shampoo composition, unless otherwise specifically indicated. All viscosities and solubilities are determined at 25° C., unless otherwise specifically indicated.

SUMMARY OF THE INVENTION

It has now been found that conditioning shampoos meeting the above objects can be achieved. In particular, it has been found that insoluble silicone conditioning agents in the form of dispersed droplets can be suspended in shampoo compositions containing anionic surfactants and relatively low levels of a shampoo-soluble cationic polymer, without the need for crystalline suspending agents or polymeric thickening agents for suspending the particles. By way of theory, and without intending to necessarily limit the invention, it is believed that the cationic polymers hereof form a net-like suspension by bridging miscelles of the anionic surfactant. The droplets of insoluble silicone become suspended within this network. It has been found that low levels of cationinc polymer can be highly effective for providing stability.

More specifically, the present invention provides a conditioning shampoo composition comprising:
(a) from about 8% to about 40%, by weight, of detersive surfactant, said composition containing at least about 5%, by weight, of anionic detersive surfactants;
(b) from about 0.05% to about 5%, by weight, of dispersed droplets of insoluble silicone;
(c) from about 0.01% to about 1.0%, by weight, of a stabilizing agent for said insoluble silicone, said stabilizing agent being a soluble cationic polymer;
(d) from about 50% to about 91.5%, by weight, water;

wherein said shampoo composition is substantially free of suspending agents selected from the group consisting of crystalline suspending agents and anionic, nonionic, and amphoteric polymeric thickening agents.

The present invention can provide shampoos with excellent conditioning efficacy, cleansing, and lathering. In addition, the present invention can result in significant cost savings in view of the elimination of conventional suspending agents such as crystalline suspending agents, which typically require separate heating and cooling steps to process the suspending agent. The present invention can also provide conditioning shampoo compositions which exhibit excellent deposition of silicone conditioning agents during use.

DETAILED DESCRIPTION OF THE INVENTION

Detersive Surfactant Component

The compositions of the present invention contain from about 8% to about 40% by weight, of detersive surfactant, preferably from about 10% to about 30%, more preferably from about 12% to about 25%. Included among the detersive surfactant hereof as a required element is an anionic detersive surfactant component. The compositions hereof can additionally contain nonionic and amphoteric surfactants, and mixtures thereof.

The anionic detersive surfactant component will generally be present at a level of at least about 5%, by weight of the composition, preferably at least about 8%, more preferably at least about 12%.

Sulfate Surfactants

The compositions hereof will preferably comprise alkyl sulfate, alkyl ethoxylated sulfate, or a mixture thereof. These materials have the respective formulae (I) $ROSO_3M$ and (II) $RO(C_2H_4O)_xSO_3M$, wherein R is alkyl or alkenyl of from about 8 to about 30 carbon atoms, x is 1 to 10, and M is H or a salt-forming cation such as ammonium, alkanolamine containing $C_1$–$C_3$ alkyl groups such as triethanolamine, and monovalent and polyvalent metals such as the alkaline and alkaline earth metals. Preferred metals include sodium, potassium, magnesium, and calcium. The cation M, of the anionic surfactant should preferably be chosen such that the anionic surfactant component is water soluble. Solubility of anionic surfactants, in general, will depend upon the particular anionic surfactants and cations chosen. As an aid to determining appropriate mixtures of anionic surfactants, the anionic surfactants should be chosen such that the Krafft temperature is about 15° C. or less, preferably about 10° C. or less, more preferably about 0° C. or less. It is also preferred that the anionic surfactant be soluble in the composition hereof.

Preferably, R has from about 10 to about 18 carbon atoms in both the alkyl and alkyl ethoxylated sulfates. The alkyl ethoxylated sulfates are typically made as condensation products of ethylene oxide and monohydric alcohols having from about 8 to about 24 carbon atoms. The alcohols can be derived from fats, e.g., coconut oil, palm kernel oil, or tallow, or can be synthetic. Such alcohols are preferably reacted with about 1 to about 10, more preferably from about 1 to about 4, most preferably from about 2 to about 3.5, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide.

The sulfate surfactant is preferably comprised of a combination of ethoxylated and nonethoxylated sulfates. The weight ratio of alkyl sulfate to alkyl ethoxylated sulfate is preferably from about 4:1 to about 1:10, more preferably from about 2:1 to about 1:8, even more preferably from about 1:1 to about 1:5, most preferably from about 1:2 to about 1:4. Weight ratios as described above are preferred for their ability to provide optimum combinations of lather, cleaning, and particulate anti-dandruff agent performance. Alkyl sulfates can provide excellent cleaning and lather performance. Alkyl ethoxylated sulfates can provide excellent cleaning performance, are mild to the skin, and can enhance deposition of the particulate anti-dandruff agent relative to alkyl sulfates.

Other Anionic Surfactants

A preferred type of anionic surfactant, especially for use in combination with anionic sulfate surfactants, are the N-acyl amino acid surfactants. N-acyl amino acid surfactants, for purposes hereof, include N-acyl hydrocarbyl acids and salts thereof, such as those represented by Formula III, as follows:

wherein: $R^1$ is a $C_8$–$C_{24}$ alkyl or alkenyl radical, preferably $C_{10}$–$C_{18}$; $R^2$ is —H, $C_1$–$C_4$ alkyl, phenyl, or —$CH_2COOM$, preferably $C_1$–$C_4$ alkyl, more preferably $C_1$–$C_2$ alkyl; $R^3$ is —$CR^4_2$— or $C_1$–$C_2$ alkoxy, wherein each $R^4$ independently is —H or $C_1$–$C_6$ alkyl or alkylester, and n is from 1 to 4, preferably 1 or 2; and M is H or a cation as previously defined, preferably an alkali metal such as sodium or potassium.

A wide variety of N-acyl acid surfactants and their synthesis are described in *Anionic Surfactants, Part 1, Surfactant Science Series, Vol. VII*, edited by Warner M. Linfield, Marcel Dekker, Inc. (New York and Basel), 1976; pp 581–617.

Especially preferred are compounds of Formula III wherein $R^2$ is methyl and $R^3$ is —$CH_2$—, and n is 1, which are known as the N-acyl sarcosinates, and acids thereof. Specific examples include lauroyl sarcosinate, myristoyl sarcosinate, cocoyl sarcosinate, and oleoyl sarcosinate, preferably in their sodium and potassium salt forms.

For the purposes of the surfactants described herein, it should be understood that the terms "alkyl" or "alkenyl" include mixtures of radicals which may contain one or more intermediate linkages such as ether or polyether linkages or non-functional substituents such as hydroxyl or halogen radicals wherein the radical remains of hydrophobic character.

Anionic detersive surfactants also include aliphatic sulfonates, such as the water-soluble salts of the organic, sulfuric acid reaction products of the general formula (IV):

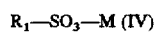

wherein $R_1$ is chosen from the group consisting of a straight or branched chain, saturated aliphatic hydrocarbon radical having from about 8 to about 24, preferably about 12 to about 18, carbon atoms; and M is a cation, as previously described. Examples are the salts of an organic sulfuric acid reaction product of a hydrocarbon of the methane series, including iso-, neo-, and n-paraffins, having about 8 to about 24 carbon atoms, preferably about 12 about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfonated $C_{12}$–$C_{18}$ paraffins (e.g. normal and secondary paraffins).

Additional examples of anionic detersive surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other synthetic anionic detersive surfactants of this variety are set forth in U.S. Pat. Nos. 2,486,921, 2,486,922, and 2,396,278.

Still other anionic detersive surfactants are in the class designated as succinates. This class includes such surface active agents as disodium N-octadecylsulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; dioctyl esters of sodium sulfosuccinic acid.

Other suitable anionic detersive surfactants also include olefin sulfonates having about 12 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxyalkanesulfonates. The sulfur trioxide can be liquid or gaseous, and is usually, but not necessarily, diluted by inert dilutents, for example, by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mixture of the above type is described more fully in the U.S. Pat. No. 3,332,880, Pflaumer and Kessler, issued Jul. 25, 1967, incorporated herein by reference.

Another class of anionic detersive surfactants are the beta-alkyloxy alkane sulfonates. These compounds have the following formula (V):

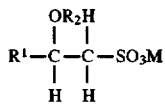

where $R_1$ is a straight chain alkyl group having from about 6 to about 20 carbon atoms, $R_2$ is a lower alkyl group having from about 1 (preferred) to about 3 carbon atoms, and M is a cation as hereinbefore described.

Many additional synthetic anionic surfactants are described in McCutcheon's Emulsifiers and Detergents, 1989 Annual, published by M. C. Publishing Co., which is incorporated herein by reference. Also U.S. Pat. No. 3,929,678, Laughlin et al., issued Dec. 30, 1975, discloses many other anionic as well as other surfactant types and is incorporated herein by reference.

Preferred anionic detersive surfactants for use in the present shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric Surfactants

Amphoteric surfactants can optionally be used in the present compositions and processes. Examples of amphoteric surfactants which can be used in the present invention include those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate.

The amphoteric surfactant hereof include the imidazolinium amphoteric surfactants such as those depicted by Formula VI:

wherein $R^1$ is $C_8$–$C_{22}$ alkyl or alkenyl, preferably $C_{12}$–$C_{16}$, $R^2$ is hydrogen or $CH_2CO_2M$, $R^3$ is $CH_2CH_2OH$ or $CH_2CH_2OCH_2CH$ COOM, $R^4$ is hydrogen, $CH_2CH_2OH$, or $CH_2CH_2OCH_2CH_2COOM$, Z is $CO_2M$ or $CH_2CO_2M$, n is 2 or 3, preferably 2, M is hydrogen or a cation as described above.

Suitable materials of this type are marketed under the tradename MIRANOL and are understood to comprise a complex mixture of species, and can exist in protonated and non-protonated species depending upon pH with respect to species that can have a hydrogen at $R^2$. The imidazolinium amphoteric surfactant hereof can be derived via an imidazolinium intermediate. However, it will be recognized by those skilled in the art that it needn't necessarily be derived via an imidazolinium.

Preferred amphoteric surfactants of Formula VII are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Specific commercial products providing the imidazolinium derivative component of the present compositions include those sold under the trade names MIRANOL C2M CONC. N.P., MIRANOL C2M CONC. O.P., MIRANOL C2M SF, MIRANOL CM SPECIAL, MIRANOL ULTRA (Miranol, Inc.); ALKATERIC 2CIP (Alkaril Chemicals);

AMPHOTERGE W-2 (Lonza, Inc.); MONATERIC CDX-38, MONATERIC CSH-32 (Mona Industries); REWOTERIC AM-2C (Rewo Chemical Group); and SCHEROTERIC MS-2 (Scher Chemicals).

Amphoteric surfactants also include aminoalkanoates of the formula (VII):

$$R\text{—}NH(CH_2)_nCOOM; \quad (VII)$$

and iminodialkanoates of the formula (VIII):

$$R\text{—}N[(CH_2)_mCOOM]_2 \quad (VIII)$$

and mixtures thereof; wherein n and m are numbers from 1 to 4, R is $C_8$–$C_{22}$ alkyl or alkenyl, and M is hydrogen or a cation as described above.

Examples of such amphoteric surfactants include n-alkylaminopropionates and n-alkyliminodipropionates. Such materials are sold under the tradename DERIPHAT by Henkel and MIRATAINE by Miranol, Inc. Specific examples include N-lauryl-beta-amino propionic acid or salts thereof, and N-lauryl-beta-imino-dipropionic acid or salts thereof.

Other amphoteric surfactants that can be used include betaine surfactants such as to be excluded include those represented by the Formula (IX):

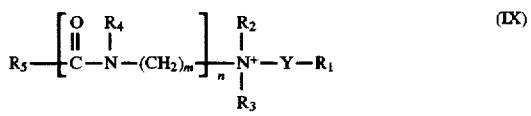

wherein:

$R_1$ is a member selected from the group consisting of

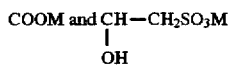

$R_2$ is $C_1$–$C_3$ alkyl or hydroxy ($C_1$–$C_3$) alkyl;

$R_3$ is $C_1$–$C_3$ alkyl or hydroxy ($C_1$–$C_3$) alkyl;

$R_4$ is a member selected from the group consisting of hydrogen and $C_1$–$C_3$ alkyl;

$R_5$ is $C_8$–$C_{20}$ alkyl or alkenyl;

Y is $C_1$–$C_3$ alkyl;

m is an integer from 2 to 7;

n is the integer 1 or 0;

M is hydrogen or a cation as described above.

Nonionic Surfactants

Nonionic detersive surfactants can also optionally be used in the present invention. Nonionic surfactants include those broadly defined as compounds produced by the condensation of alkylene oxide groups (hydrophilic in nature) with an organic hydrophobic compound, which may be aliphatic or alkyl aromatic in nature. Examples of preferred classes of nonionic detersive surfactants are:

1. The polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol.

2. Those derived from the condensation of ethylene oxide with the product resulting from the reaction of propylene oxide and ethylene diamine products.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

$$R_1 R_2 R_3 N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals, the arrow in the formula is a conventional representation of a semipolar bond.

5. Long chain tertiary phosphine oxides corresponding to the following general formula:

$$RR'R''P \rightarrow O$$

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R'' are each alkyl or monohydroxyalkyl groups containing from about 1 to about 3 carbon atoms.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety.

7. Alkyl polysaccharide (APS) surfactants such as the alkyl polyglycosides. Such surfactants are described in U.S. Pat. No. 4,565,647, Llenado, issued Jan. 21, 1986, incorporated herein by reference, which discloses APS surfactants having a hydrophobic group with about 6 to about 30 carbon atoms and polysaccharide (e.g., polyglycoside) as the hydrophilic group. Optionally, there can be a polyalkylene-oxide group joining the hydrophobic and hydrophilic moieties. The alkyl group (i.e., the hydrophobic moiety) can be saturated or unsaturated, branched or unbranched, and unsubstituted or substituted (e.g., with hydroxy or cyclic rings).

8. Polyethylene glycol (PEG) glyceryl fatty esters, such as those of the formula $R(O)OCH_2CH(OH)CH_2(OCH_2CH2)_nOH$ wherein n is from about 5 to about 200, preferably from about 20 to about 100, and R is an aliphatic hydrocarbyl having from about 8 to about 20 carbon atoms.

9. Polyhydroxy fatty acid amides of the formula:

wherein: $R^1$ is $H$, $C_1$–$C_4$ hydrocarbyl, 2-hydroxy ethyl, 2-hydroxy propyl, or a mixture thereof, preferably $C_1$–$C_4$ alkyl, more preferably C₁ or C₂ alkyl, most preferably C₁ alkyl (i.e., methyl); and R² is a C₅-C₃₁ hydrocarbyl moiety, preferably straight chain C₇-C₁₉ alkyl or alkenyl, more preferably straight chain C₉-C₁₇ alkyl or alkenyl, most preferably straight chain C₁₁-C₁₅ alkyl or alkenyl, or mixture thereof; and Z is a polyhydroxyhydrocarbyl moiety having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —CH₂—(CHOH)ₙ—CH₂OH, —CH(CH₂OH)—(CHOH)ₙ₋₁—CH₂OH, —CH₂—(CHOH)₂(CHOR')(CHOH)-CH₂OH, where n is an integer from 3 to 5, inclusive, and R' is H or a cyclic or aliphatic monosaccharide, and alkoxylated derivatives thereof. Most preferred are glycityls wherein n is 4, particularly —CH₂—(CHOH)₄—CH₂OH.

In the above formula, R¹ can be, for example, N-methyl, N-ethyl, N-propyl, N-isopropyl, N-butyl, N-2-hydroxy ethyl, or N-2-hydroxy propyl.

R²—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

Polyhydroxy fatty acid amides are disclosed, for example, in G.B. Patent Specification 809,060, published Feb. 18, 1959, by Thomas Hedley & Co., Ltd., U.S. Pat. No. 2,965,576, issued Dec. 20, 1960 to E. R. Wilson, and U.S. Pat. No. 2,703,798, Anthony M. Schwartz, issued Mar. 8, 1955, and U.S. Pat. No. 1,985,424, issued Dec. 25, 1934 to Piggott, each of which is incorporated herein by reference.

When used, the optional amphoteric and nonionic surfactants are typically present at levels of from about 0.05% to about 20%, more typically from about 0.1% to about 10%, preferably from about 0.5% to about 5%, although higher or lower levels can be used.

Insoluble Silicone Conditioning Agent

The insoluble silicone conditioning agents hereof includes any silicone fluid or gum which is useful for conditioning hair or skin. The silicone conditioning agents include polyalkyl siloxanes, polyaryl siloxanes, polyalkylaryl siloxanes, polyether siloxane copolymers, and mixtures thereof. Other insoluble silicone fluids having conditioning properties can also be used. The silicone conditioning agent will preferably be nonvolatile. The term "nonvolatile" as used herein shall mean that the material has a boiling point of at least about 260° C., preferably at least about 275° C., more preferably at least about 300° C. Such materials exhibit very low or no significant vapor pressure at ambient conditions. The term "silicone fluid" shall mean flowable silicone materials having a viscosity of less than 1,000,000 centistokes at 25° C. The term silicone gum shall mean flowable silicone materials having a viscosity of 1,000,000 centistokes at 25° C., or greater. The viscosity can be measured by means of a glass capillary viscometer as set forth in Dow Corning Corporate Test Method CTM0004, Jul. 20, 1970, or equivalent. The insoluble silicone conditioning agent for use herein will preferably have an average viscosity of from about 15 to about 2,000,000 centistokes at 25° C., more preferably from about 1,000 to about 1,800,000, even more preferably from about 10,000 to about 1,500,000, most preferably from about 50,000 to about 1,500,000. By average viscosity of the silicone conditioning agent what is meant is the viscosity of the combined insoluble silicone conditioning agent materials, including both fluids and gums, that may be used in admixture.

Preferred silicone conditioning agents hereof also include siloxanes with the following structure:

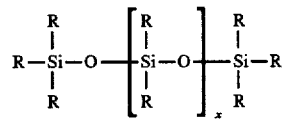

wherein each R independently is alkyl, aryl, or alkylaryl, alkoxy, alkylamino, hydroxy alkyl, and x is an integer from about 7 to about 8,000 may be used. The alkyl portions of the substituents preferably have from 1 to about 10 carbon atoms, except with regard to the alkyaryls which preferably have a total of from about 6 to about 10 carbons and from 1 to about 4 carbon atoms in the alkyl portion.

The groups substituted on the siloxane chain (R) may have any structure as long as the resulting silicones remain as liquids at room temperature, are neither toxic nor otherwise harmful when applied to the hair, are compatible with the other components of the composition, are chemically stable under normal use and storage conditions, and are capable of being deposited on and of conditioning hair.

Preferred R groups include methoxy, ethoxy, propoxy, methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. These siloxanes are available, for example, from the General Electric Company in their Viscasil® and SF 96 series, and from Dow Corning in their Dow Corning 200 series.

The polyalkylaryl siloxane fluids that may be used, include, for example, polymethylphenylsiloxanes. These siloxanes are available, for example, from the General Electric Company as SF 1075 methyl phenyl fluid or from Dow Corning as 556 Cosmetic Grade Fluid.

Especially preferred, for enhancing the shine characteristics of hair, are highly arylated silicones, such as highly phenylated polyethyl silicone having refractive indices of about 1.46 or higher, especially about 1.52 or higher. When these high refractive index silicones are used, they are preferably mixed with a spreading agent, such as a surfactant or a silicone resin, to decrease the surface tension and enhance the film forming ability of the material.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level should be sufficiently low to prevent solubility in the composition hereof.

References disclosing suitable silicone fluids include U.S. Pat. Nos. 2,826,551, Geen; 3,964,500, Drakoff, issued Jun. 22, 1976; 4,364,837, Pader; and British Patent 849,433, Woolston. All of these patents are incorporated herein by reference. Also incorporated herein by reference is Silicon Compounds distributed by Petrarch Systems, Inc., 1984. This reference provides an extensive (though not exclusive) listing of suitable silicone fluids.

Another silicone hair conditioning material that can be especially useful in the silicone conditioning agents is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. All of these described references are incorporated herein by reference. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Preferably the silicone hair conditioning agent comprises a mixture of a polydimethylsiloxane gum, having a viscosity greater than 1,000,000 centistokes and polydimethylsiloxane fluid having a viscosity of from about 10 centistokes to about 100,000 centistokes, wherein the ratio of gum to fluid is from about 30:70 to about 70:30, preferably from about 40:60 to about 60:40.

The silicone conditioning agent will be present in the form of droplets dispersed throughout the aqueous phase of the shampoo. The silicone can be incorporated into a solution of the surfactant and water, such as but not limited to the anionic detersive surfactant hereof, as a neat solution, followed by mechanical mixing (shear mixing) to form emulsify the silicone. Alternately, the silicone can be emulsified prior to incorporation into the shampoo. Anionic, cationic, nonionic, and amphoteric surfactants can be used as the emulsifying agent. Suitable surfactants for this purpose include the surfactants described previously in this document. Preferably the silicone is preemulsified with an anionic surfactant (preferably alkyl sulfate, alkyl ethoxylated sulfate, or a combination thereof) prior to incorporation into the shampoo.

The level of silicone conditioning agent in the shampoo should be from about 0.05% to about 5%, by weight of the composition, preferably from about 0.1% to about 3%, most preferably from about 0.25% to about 2%. The number average particle size of the silicone droplets can be from submicron size to about 50 microns, preferably at least about 0.5 microns, more preferably at least about 1 micron, even more preferably at least about 2 microns, most preferably at least about 3 microns. Number average particle size is preferably no greater than about 35 microns, more preferably no greater than about 25 microns.

Cationic Polymer

The compositions hereof contain at least about 0.01%, by weight, of a stabilizing agent for the insoluble silicone conditioning agent, preferably from about 0.01% to about 1%, more preferably from about 0.02% to about 0.5%, most preferably from about 0.02% to about 0.1%. Lower levels are contemplated as long as stability benefits are obtained. The stabilizing agent hereof is a shampoo soluble cationic polymer. It has been found that very low levels of such cationic polymer can effectively aid in suspension stability of the insoluble silicone conditioning agent in the present shampoo compositions, with substantially reduced deposition trade-offs versus conventional suspension technologies. By "shampoo soluble" what is meant is that the cationic polymer is present in the shampoo in solubilized form at a level sufficient to aid in suspension of the insoluble silicone conditioning agent. The shampoo soluble cationic polymers can exist in free ion form or as coacervates formed with the anionic surfactant.

The cationic polymers hereof will generally have a weight average molecular weight which is at least about 200,000, typically at least about 400,000, and less than about 10 million. Preferably, the molecular weight is from about 400,000 to about 5 million, more preferably about 800,000 to about 2 million. The cationic polymers will have cationic nitrogen-containing moieties such as quaternary ammonium or cationic amino moieties, or a mixture thereof.

The cationic charge density is preferably at least about 0.3 meq/gram, more preferably at least about 0.6 meq/gram, even more preferably at least about 1.0 meq/gram, most preferably at least about 1.2 meq/gram. The cationic charge density in general will be about 4 meq/gram or less, more generally about 3.0 meq/gram or less. Cationic charge density of the cationic polymer can be determined according to the Kjeldahl Method. Those skilled in the art will recognize that the charge density of amino-containing polymers in the final product may vary depending upon pH and the isoelectric point of the amino groups. The charge density should be within the above limits at the pH of intended use.

Any anionic counterions can be utilized for the cationic polymers so long as the water solubility criteria is met. Suitable counterions include halides (e.g., Cl, Br, I, or F, preferably Cl, Br, or I), sulfate, and methylsulfate. Others can also be used, as this list is not intended to be exhaustive.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in the CTFA Cosmetic Ingredient Dictionary, 3rd edition, edited by Estrin, Crosley, and Haynes, (The Cosmetic, Toiletry, and Fragrance Association, Inc., Washington, D.C., 1982).

Suitable cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the shampoo. In general, secondary and tertiary amines, especially tertiary amines, are preferred.

Amine-substituted vinyl monomers can be polymerized in the amine form, and then optionally can be converted to ammonium by a quaternization reaction. Amines can also be similarly quaternized subsequent to formation of the polymer. For example, tertiary amine functionalities can be quaternized by reaction with a salt of the formula R'X wherein R' is a short chain alkyl, preferably a $C_1$–$C_7$ alkyl, more preferably a $C_1$–$C_3$ alkyl, and X is an anion which forms a water soluble salt with the quaternized ammonium.

Suitable cationic amino and quaternary ammonium monomers include, for example, vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$–$C_3$ alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Wyandotte Corp. (Parsippany, N.J., USA) under the LUVIQUAT tradename (e.g., LUVIQUAT FC 370); copolymers of 1-vinyl-2-pyrrolidone and dimethylaminoethyl methacrylate (referred to in the industry by CTFA as Polyquaternium-11) such as those commercially available from ISP Corporation (Wayne, N.J., USA) under the GAFQUAT tradename (e.g., GAFQUAT 755N); cationic diallyl quaternary ammonium-containing polymers, including, for example, dimethyldiallylammonium chloride homopolymer and copolymers of acrylamide and dimethyldiallylammonium chloride, referred to in the industry (CTFA) as Polyquaternium 6 and Polyquaternium 7, respectively; and mineral acid salts of amino-alkyl esters of homo- and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

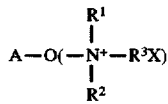

wherein:

A is an an hydroglucose residual group, such as a starch or cellulose an hydroglucose residual, R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer JR$^{TN}$, LR$^{TN}$, and LK$^{TN}$ series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted opoxide, referred to in the industry (CTFA) as Polyquaternium 24. These materials are available from Amerchol Corp. (Edison, N.J., USA) under the tradename Polymer LM-200.

Other cationic polymers that can be used include cationic guar gum derivatives, such as guar hydroxypropyltrimonium chloride (commercially available from Celanese Corp. in their Jaguar® series). Other materials include quaternary nitrogen-containing cellulose ethers (e.g., as described in U.S. Pat. No. 3,962,418, incorporated by reference herein), and copolymers of etherified cellulose and starch (e.g., as described in U.S. Pat. No. 3,958,581, incorporated by reference herein). Especially preferred cationic polymers include Polyquaternium 10.

Substantially Free of Conventional Suspending Agents

The present compositions are preferably substantially free of crystalline suspending agents and anionic, amphoteric and nonionic polymeric thickening agents. In general, by "substantially free" what is meant is that the level of such suspending agents be about 0.5% or less, more preferably about 0.3% or less, even more preferably about 0.1% or less, most preferably 0% or no more than about 0.05%.

Crystalline suspending agents include long chain (e.g., $C_8$–$C_{22}$ preferably $C_{14}$–$C_{22}$, more preferably $C_{16}$–$C_{22}$) aliphatic groups, i.e., long chain acyl derivative materials and long chain amine oxides, as well as mixtures of such materials. Included are ethylene glycol long chain esters, alkanol amides of long chain fatty acids, long chain esters of long chain fatty acids, glyceryl long chain esters, long chain esters of long chain alkanolamides, and long chain alkyl dimethyl amine oxides, and mixtures thereof. Common suspending agents include, for example, ethylene glycol esters of fatty acids preferably having from about 14 to about 22 carbon atoms, more preferably 16–22 carbon atoms. Other suspending agents include $C_{16}$–C22 alkanol amides of fatty acids and alkanol amides such as stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate); glyceryl esters (e.g., glyceryl distearate) and long chain esters of long chain alkanol amides (e.g., stearamide diethanolamide distearate, stearamide monoethanolamide stearate). Crystalline suspending agents also include long chain amine oxides such as alkyl ($C_{16}$–$C_{22}$) dimethyl amine oxides, e.g., stearyl dimethyl amine oxide. Other crystalline suspending agents include long chain acyl derivatives such as N,N-dihydrocarbyl ($C_{12}$–$C_{22}$) amido benzoic acid and soluble salts thereof (e.g., Na and K salts).

Polymeric suspending agents include any anionic, nonionic, or amphoteric polymeric materials that function as thickening agents in the present aqueous surfactant compositions. These include, for example, carboxyvinyl polymers, such as copolymers of acrylic acid crosslinked with polyallylsucrose as described in U.S. Pat. No. 2,798,053, Brown, issued Jul. 2, 1957, incorporated herein by reference. A carboxyvinyl polymer is an interpolymer of a monomeric mixture comprising a monomeric olefinically unsaturated carboxylic acid, and generally from about 0.01% to about 10% by weight of the total monomers of a polyether of a polyhydric alcohol, which polyhydric alcohol contains at least four carbon atoms to which are attached at least three hydroxyl groups, the polyether containing more than one alkenyl group per molecule.

Other polymeric suspending agents include those that can impart a gel-like viscosity to the composition, such as water soluble or colloidally water soluble polymers like cellulose ethers (e.g., carboxymethylcellulose hydroxyethyl cellulose), guar gum, xanthan gum, polyvinyl alcohol, polyvinyl pyrrolidone, hydroxypropyl guar gum, starch and starch derivatives. Other polymeric thickening agents to be excluded hereunder include acrylic acid and/or acrylate polymers, particularly the acrylic acid/$C_{10}$–$C_{30}$ acrylates crosslinked polymers such as the carbomer polymers. Polymeric suspending agents also include hydrophobically modified water soluble polymers, especially $C_{12}$–$C_{22}$ alkyl substituted cellulose polymers such as hydroxyethyl cellulose. Such polymers can be combined with surfactants or water soluble polymers to achieve a thickening, and consequently suspending, effect. Such polymers are disclosed for example in U.S. Pat. Nos. 5,106,609, issued Apr. 21, 1992 to Bolich et al., 5,100,658, issued Mar. 31, 1992 to Bolich et al., 5,104,646, issued Apr. 14, 1992 to Bolich et al., and 5,100,657, issued Mar. 31, 1992 to Ansher-Jackson et al., all of which are incorporated herein by reference.

Water

The compositions of the present invention comprise from about 50% to about 91.5%, preferably from about 55% to about 90%, more preferably from about 60% to about 85%, by weight, of water.

The pH of the compositions hereof is not generally critical and may be in the range of from 2 to about 10, preferably from about 3 to about 9, more preferably from about 4 to about 8, most preferably from about 5.5 to about 7.5.

Optional Conditioning Agents

Conditioning agents for the skin or hair may optionally be added to the compositions hereof. The conditioning agents for use herein include shampoo soluble conditioning agents and crystalline conditioning agents.

Soluble conditioning agents can include soluble silicone fluids, such as polyalkoxy silicones (e.g. polyethylene oxide and poly(ethylene/propylene) oxide-modified polyalkylsiloxanes, preferably polymethyl siloxanes, such as dimethicone copolyol), $C_8$–$C_{18}$ fatty acids, $C_1$–$C_4$ esters of $C_8$–$C_{18}$ fatty acids, glycerine and other polyhydric alcohols, such as $C_3$–$C_6$ di-hydric alcohols and polyethylene glycol and polyethylene/polypropylene glycol polymers.

Various of these conditioning agents may be soluble in the compositions up to a certain level, depending upon the particular ingredient chosen and the choice and levels of additional ingredients in the composition, particularly the type and amount of other surfactants, salts and the about of water. The amount of such ingredients should preferably be chosen such that the entire amount added is soluble in the composition.

The polyether siloxane copolymers that may be used include, for example, a polyethylene oxide modified polydimethylsiloxane (e.g., Dow Corning DC-1248) although propylene oxide or mixtures of ethylene oxide and propylene oxide may also be used. The ethylene oxide and polypropylene oxide level must be sufficiently high to provide solubility in the composition hereof.

Cationic surfactants can also be used as optional ingredients. Cationic surfactants useful in compositions of the present invention, particularly the conditioner compositions, contain amino or quaternary ammonium hydrophilic moieties which are positively charged when dissolved in the aqueous composition of the present invention. Cationic surfactants among those useful herein are disclosed in the following documents, all incorporated by reference herein: M. C. Publishing Co., *McCutcheon's, Detergents &* *Emulsifiers*, (North American edition 1979); Schwartz, et al., *Surface Active Agents, Their Chemistry and Technology*, New York: interscience Publishers, 1949; U.S. Pat. Nos. 3,155,591, Hilfer, issued Nov. 3, 1964; 3,929,678, Laughlin, et al., issued Dec. 30, 1975; 3,959,461, Bailey, et al., issued May 25, 1976; and 4,387,090, Bolich, Jr., issued Jun. 7, 1983.

Among the quaternary ammonium-containing cationic surfactant materials useful herein are those of the general formula:

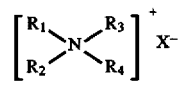

wherein $R_1$–$R_4$ are independently an aliphatic group of from about 1 to about 22 carbon atoms, aryl, or an alkoxy, polyoxyalkylene, alkylamido, hydroxyalkyl, or alkylaryl group having from about 1 to about 22 carbon atoms; and X is an anion selected from halogen (especially chlorine), acetate, phosphate, nitrate and alkylsulfate (preferably $C_1$–$C_3$ alkyl) radicals. The aliphatic groups may contain, in addition to carbon and hydrogen atoms, ether linkages, and other groups such as amino groups. The longer chain aliphatic groups, e.g., those of about 12 carbons, or higher, can be saturated or unsaturated.

Quaternary ammonium salts include dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Other cationic surfactants include those wherein at least one of the $R_1$–$R_4$ radicals contains one or more hydrophilic moieties selected from alkoxy (preferably $C_1$–$C_3$ alkoxy), polyoxyalkylene (preferably $C_1$–$C_3$ polyoxyalkylene), alkylamido, hydroxyalkyl, alkylester, and combinations thereof. Optionally, the cationic conditioning surfactant contains from 2 to about 10 nonionic hydrophile moieties in the $R_1$–$R_4$ groups. For purposes herein, each hydrophilic amido, alkoxy, hydroxyalkyl, alkylester, alkylamido or other unit is considered to be a distinct nonionic hydrophile moiety.

Other quaternary ammonium salts useful herein are diquaternary ammonium salts, such as tallow propane diammonium dichloride.

Salts of primary, secondary and tertiary fatty amines are also suitable cationic surfactant materials. The alkyl groups of such amines preferably have from about 12 to about 22 carbon atoms, and may be substituted or unsubstituted. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

The shampoos hereof can also optionally comprise additional, nonsilicone, insoluble conditioning oils, such as hydrocarbons, fatty alcohols, and fatty acid esters. Preferred of the additional insoluble conditioning agents include $C_{10}$ or higher hydrocarbons such as polybutene, mineral oil, petrolatum, and isostearoyl stearate.

Particulate Antidandruff Agent

The shampoo compositions may optionally contain one or more particulate antidandruff agents. A safe and effective amount of antidandruff active for control of dandruff of the scalp is preferably used. Particulate antidandruff agents include, for example, sulfur, selenium sulfide, and pyridinethione salts. Preferred are heavy metal salts of 1-hydroxy-2-pyridinethione and selenium disulfide. The particulate antidandruff agents are in crystalline form and are insoluble in the compositions. In general, particulate antidandruff agents can be present at levels of about 0.1% to about 5%, preferably from about 0.3% to about 2%, by weight of the composition. The particular amount used is not critical as long as a safe and effective amount is used for controlling dandruff when the composition is used to shampoo the hair.

The particulate anti-dandruff agent preferably has a number average particle size of from about 0.35 microns to about 5 microns, more preferably from about 0.40 microns to about 3 microns, most preferably from about 0.45 microns to about 2 microns. The number average particle size is determined with a forward laser light scattering device which applies the Fraunhofer and Mie light scattering theories using a helium neon laser beam (632.8 nm) and 50 watt tungsten lamp, or equivalent. An example of suitable equipment includes the Horiba LA 910 light scattering particle size analyzer (Horiba Ltd., Kyoto, Japan). Preferably, at least about 50% of the particles will have a particle size within the above numerical range, more preferably at least about 75%.

Selenium sulfide is a staple item of commerce. Selenium sulfide is generally regarded as a compound having one mole of selenium and two moles of sulfur. However, it may take the form of a cyclic structure, $Se_xS_y$, wherein $x+y=8$.

U.S. Pat. Nos. 2,694,668, Baldwin et al., issued Nov. 16, 1954; 3,152,046, Kapral, issued Oct. 6, 1984; 4,089,945, Brinkman, issued May 16, 1978; and 4,885,107, Wetzel, issued Dec. 12, 1989, all incorporated herein by reference, disclose selenium disulfide as an active ingredient in antidandruff shampoo compositions.

If used, selenium sulfide is typically present in the shampoo compositions of this invention at a level of from about 0.1% to about 5.0%, preferably from about 0.3% to about 2.5%, more preferably from about 0.5% to about 1.5%, by weight of the composition.

Preferred pyridinethione antidandruff agents are water insoluble 1-hydroxy-2-pyridinethione salts. Preferred salts are formed from heavy metals such as zinc, tin, cadmium, magnesium, aluminum and zirconium. The most preferred metal is zinc. The most preferred active is the zinc salt of 1-hydroxy-2-pyridinethione, often referred to as zinc pyridinethione (ZPT). Other cations, such as sodium, may also be used. These types of antidandruff agents are well known in the art. Pyridinethione salts are disclosed for use in antidandruff shampoos in U.S. Pat. Nos. 2,809,971, Bernstein, issued Oct. 15, 1957; 3,236,733, Karsten et al., issued Feb. 22, 1966; 3,753,196 Parran, issued Aug. 21, 1973; 3,761,418, Parran, issued Sep. 25, 1973; 4,345,080, Bolich, issued Aug. 17, 1982; 4,323,683, Bolich et al., issued Apr. 6, 1982; 4,379,753, Bolich, issued Apr. 12, 1983; and 4,470,982, Winkler, issued Sep. 11, 1984; all incorporated herein by reference.

The pyridinethione salts are preferably used at a level of from about 0.1% to about 3%, more preferably about 0.3% to about 2%, by weight of the shampoo composition.

Other particulate antidandruff actives include sulfur. Sulfur is typically used as an antidandruff agent at a level of from about 1% to about 5%, more preferably from about 2% to about 5%, by weight of the composition.

Small particle size anti-dandruff agents can be obtained from commercial suppliers or can be made by reducing larger particle size materials to the desired size by shear milling.

The order in which the cationic polymers, anionic surfactant, and particulate anti-dandruff agent are incorporated into the final composition has been found to affect the final product. Either the cationic polymer or the particulate anti-dandruff agent (but not both) should preferably be admixed in water with anionic surfactant before the cationic polymer and anti-dandruff agent are admixed together under aqueous conditions, during preparation of the composition. In other words, when the particulate anti-dandruff agent and cationic polymer exist together under aqueous conditions (i.e., in water) it should be in the presence of anionic surfactant. This is especially important for negatively charged anti-dandruff particles or anti-dandruff particles dispersed with a negatively charged dispersing aid, e.g., an anionic polymer or dispersing aid. It is also contemplated within the scope of the invention and the above description to prepare the composition under a variety of alternate conditions including admixing the cationic polymer and antidandruff agent under dry conditions, and then adding this mixture to an aqueous anionic surfactant solution. It is especially preferred to prepare an intermediate aqueous mixture containing the particulate anti-dandruff and anionic surfactant, and then add the cationic polymer.

In a preferred embodiment hereof, the compositions of the invention are made by the steps:

(a) preparing an aqueous mixture comprising:
  (i) anionic surfactant, (ii) water, and (iii) either the particulate anti-dandruff agent or the cationic polymer, preferably the particulate anti-dandruff agent; and
(b) mixing into the aqueous mixture of (a) either the particulate anti-dandruff agent or the cationic polymer, whichever remains after step (a).

Optional Ingredients

A variety of other optional ingredients are described below. The description below is exemplary in nature.

Such optional ingredients include, for example, preservatives such as benzyl alcohol, methyl paraben, propyl paraben, DMDM hydantoin, and imidazolidinyl urea; salts such as sodium chloride, sodium sulfate; viscosity modifiers, such as ammonium xylene sulfonate; propylene glycol; polyvinyl alcohol; ethyl alcohol; pH adjusting agents such as citric acid, succinic acid, phosphoric acid, and salts thereof, sodium hydroxide, sodium carbonate, etc.; foam boosters, such as $C_8$–$C_{18}$ mono- and di-ethanol amides, especially coco mono- and di-ethanol amides; perfumes; and dyes. These optional ingredients are typically used at levels of from about 0.01% to about 10% of the composition. This list of optional ingredients is not meant to be exclusive, as a wide variety of other optional components can be utilized.

METHOD OF USE

The present compositions are used in a conventional manner for cleaning and conditioning the scalp and hair. The compositions hereof can also be affective for cleaning and conditioning the skin. An effective amount of the composition, typically from about 1 g to about 20 g of the composition, for cleaning hair, scalp, or other region of the body, is applied to the hair, scalp, or other region that has preferably been wetted, generally with water, and then rinsed off. Application to the hair typically includes working the composition through the hair and scalp such that most or all of the hair, scalp, or skin to be treated is contacted with the composition.

EXAMPLES

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLES I–XX

The following examples exemplify shampoo compositions of the present invention.

The compositions are prepared as follows.

For Examples I to XX, if fatty alcohol and/or cocomonoethanol amide (CMEA) are used about one-third to all of the total alkyl sulfate surfactant (ammonium laureth-3 sulfate (added as a 25 wt. % solution) and/or ammonium lauryl sulfate (added as a 25 wt. % solution)) is added to a jacketed mix tank and heated to about 65° C. with slow agitation to form a surfactant solution. If neither fatty alcohol nor CMEA are used, the surfactants are added to a tank without heating. In both situations, next add the preservative to the tank and allow it to disperse. If it has been heated, as set forth above, the mixture is then passed through a heat exchanger where it is cooled to about 35° C. and collected in a finishing tank. For examples utilizing a 60/40 mixture of dimethicone gum and fluid as the dimethicone component, a silicone premix is prepared by adding 70% (by weight, premix basis) of the dimethicone, blending 29%, (by weight, premix basis) of an ammonium laureth-3 sulfate aqueous solution (25 wt. % active) and 1% (by weight, premix basis) Sodium Chloride, on a silicone premix weight basis, to a high shear mixing vessel and mixing for about 30 minutes or until a dimethicone particle size of about 5 to about 10 microns is achieved. The remainder of the ammonium laureth sulfate, lauryl sulfate and other ingredients including the dimethicone component, are added to the finishing tank with agitation to ensure a homogeneous mixture. Polyquaternium 10 is dispersed in water as a 1% aqueous solution before addition to the final mix. Once all ingredients have been added, ammonium xylene sulfonate or additional sodium sulfate may be added to the mixture to thin or thicken respectively to achieve a desired product viscosity. Preferred viscosities range from about 2500 to about 6000 cS at 25° C. (as measured by a Wells-Brookfield cone and plate viscometer at a shear rate of 15/s).

The compositions of the Examples can provide excellent in-use hair cleaning, lather, and conditioning.

| Component (%, by weight, of composition) | Example No. | | | | |
|---|---|---|---|---|---|
| | I | II | III | IV | V |
| Ammonium Laureth (3) Sulfate | 13.5 | 13.5 | 16 | 8 | 16 |
| Ammonium Lauryl Sulfate | 4.5 | 4.5 | 1.5 | 8 | 3 |
| Sodium Lauryl Sarcosinate | 1.5 | 2 | 3.75 | 2.5 | 0 |
| Cocoamidopropyl Betaine | 1.5 | 1 | 0 | 0 | 2 |
| Sodium Sulfate | 0.8 | 0.8 | 0/8 | 0.8 | 0.8 |
| Polyquaternium 10[1] | 0.025 | 0.025 | 0.02 | 0.05 | 0.05 |
| Dimethicone[2] | 0.75 | 0.5 | 1 | 1 | 1.5 |
| Perfume Solution | 0.65 | 0.65 | 0.4 | 0.5 | 0.25 |

-continued

| | | | | | |
|---|---|---|---|---|---|
| DMDM Hydantoin | 0.2 | 0.2 | 0.3 | 0.3 | 0.3 |
| Color Solution (ppm) | 10 | 10 | 10 | 20 | 20 |
| Water | qs | qs | qs | qs | qs |

| Component (%, by weight, of composition) | Example No. | | | | |
|---|---|---|---|---|---|
| | VI | VII | VIII | IX | X |
| Ammonium Laureth (3) Sulfate | 11.5 | 14.5 | 16 | 6 | 16 |
| Ammonium Lauryl Sulfate | 4.5 | 2.5 | 3.5 | 8 | 2 |
| Sodium Lauryl Sarcosinate | 1.5 | 2 | 3.75 | 2.5 | 2 |
| Cocoamidopropyl Betaine | 1.5 | 1.5 | 0 | 0 | 1.5 |
| Sodium Sulfate | 0.8 | 0.8 | 0.8 | 0.8 | 0.8 |
| Coconut (C12–C14) Fatty Alcohol | 0.2 | 0 | 0.35 | 0 | 0 |
| Polyquaternium 10[1] | 0.025 | 0.02 | 0.025 | 0.05 | 0.75 |
| Dimethicone[3] | 1 | 0.5 | 1 | .75 | 1.5 |
| Perfume Solution | 0.65 | 0.65 | 0.4 | 0.5 | 0.25 |
| DMDM Hydantoin | 0.2 | 0.2 | 0.3 | 0.3 | 0.3 |
| Color Solution (ppm) | 10 | 10 | 10 | 20 | 20 |
| Water | qs | qs | qs | qs | qs |

| Component (%, by weight, of composition) | Example No. | | | | |
|---|---|---|---|---|---|
| | XI | XII | XIII | XIV | XV |
| Ammonium Laureth (3) Sulfate | 18 | 0 | 15 | 15 | 10 |
| Ammonium Lauryl Sulfate | 0 | 12 | 3 | 5 | 5 |
| Sodium Lauryl Sarcosinate | 3 | 0 | 2.3 | 1 | 5 |
| Cocoamidopropyl Betaine | 1 | 3 | 0 | 1.5 | 0 |
| Sodium Sulfate | 0.8 | 0.8 | 0.8 | 0.8 | 0.8 |
| Coconut (C12–C14) Fatty Alcohol | 0.2 | 0.2 | 0 | 0.35 | 0 |
| Polyquaternium 10[1] | 0.1 | 0.2 | 0.5 | 0.2 | 0.2 |
| Dimethicone[4] | .75 | 0.5 | 1 | .75 | 1.5 |
| Perfume Solution | 0.9 | 0.35 | 0.3 | 0.7 | 1.1 |
| DMDM Hydantoin | 0.2 | 0.2 | 0.4 | 0.4 | 0.4 |
| Color Solution (ppm) | 10 | 10 | 10 | 20 | 20 |
| Water | qs | qs | qs | qs | qs |

| Component (%, by weight, of composition) | Example No. | | | | |
|---|---|---|---|---|---|
| | XVI | XVII | XVIII | XIX | XX |
| Ammonium Laureth (3) Sulfate | 18 | 0 | 15 | 13 | 10 |
| Ammonium Lauryl Sulfate | 0 | 12 | 3 | 5 | 5 |
| Sodium Lauryl Sarcosinate | 3 | 0 | 2.3 | 1 | 5 |
| CMEA | 0.75 | 3 | 1.5 | 2 | 1 |
| Cocoamidopropyl Betaine | 1 | 0 | 0 | 1.5 | 0 |
| Sodium Sulfate | 0.8 | 0.8 | 0.8 | 0.8 | 0.8 |
| Coconut (C12–C14) Fatty Alcohol | 0.2 | 0.2 | 0 | 0.35 | 0 |
| Polyquaternium 10[1] | 0.1 | 0.2 | 0.25 | 0.2 | 0.2 |
| Dimethicone[2] | 1 | 0.5 | 1 | 0.75 | 1.5 |
| Perfume Solution | 0.9 | 0.35 | 0.3 | 0.7 | 1.1 |
| DMDM Hydantoin | 0.2 | 0.2 | 0.4 | 0.4 | 0.4 |
| Color Solution (ppm) | 10 | 10 | 10 | 20 | 20 |
| Water | qs | qs | qs | qs | qs |

[1] UCARE Polymer JR-30M, commercially available from Union Carbide Corporation.
[2] 60/40 wt. percent mixture of Dimethicone Fluid (General Electric SF-96, 350 cS)/Dimethicone Gum (General Electric; SF-76).
[3] DC 200 fluid (12,500 centistoke), available from Dow Corning (Midland, Michigan, USA), neat solution.
[4] DC 1664, a dimethicone fluid in aqueous emulsion (nonionic emulsifier), commercially available from Dow Corning Corp. (Midland, Michigan, USA).

EXAMPLES XXI–XXXII

The following comparative examples demonstrate benefits of the shampoo compositions of the present invention.

The compositions were prepared as described above with regard to Examples I–XX. The products were adjusted to a product viscosity of about 4000 cS at 25° C. The products were stability tested by packaging them in covered, eight ounce clear bottles and subjecting them to a constant temperature of 49° C. The formulas tested are shown below.

| Component | Example No. | | |
|---|---|---|---|
| (%, by weight, of composition) | XXI | XXII | XXIII |
| Ammonium Laureth (3) Sulfate | 15.0 | 15.0 | 15.0 |
| Ammonium Lauryl Sulfate | 5.0 | 5.0 | 5.0 |
| Betaine | 1.5 | 1.5 | 1.5 |
| Sodium Sulfate | 0.8 | 0.8 | 0.8 |
| Polyquaternium 10¹ | 0.0 | 0.025 | 0.05 |
| Dow Corning 200 Fluid (12,5000 cs) | 1.0 | 1.0 | 1.0 |
| Perfume Solution | 0.65 | 0.65 | 0.65 |
| DMDM Hydantoin | 0.2 | 0.2 | 0.2 |
| Color Solution (ppm) | 10 | 10 | 10 |
| Water | qs | qs | qs |

| Component | Example No | | |
|---|---|---|---|
| (%, by weight, of composition) | XXIV | XXV | XXVI |
| Ammonium Laureth (3) Sulfate | 15.0 | 15.0 | 15.0 |
| Ammonium Lauryl Sulfate | 5.0 | 5.0 | 5.0 |
| Betaine | 1.5 | 1.5 | 1.5 |
| Sodium Sulfate | 0.8 | 0.8 | 0.8 |
| Polyquaternium 10 | 0 | 0.025 | 0.05 |
| Dow Corning 200 Fluid (350 cs) | 1.0 | 1.0 | 1.0 |
| Perfume Solution | 0.65 | 0.65 | 0.65 |
| DMDM Hydantoin | 0.2 | 0.2 | 0.2 |
| Color Solution (ppm) | 10 | 10 | 10 |
| Water | qs | qs | qs |

| Component | Example No. | | |
|---|---|---|---|
| (%, by weight, of composition) | XXVII | XXVIII | XXIX |
| Ammonium Laureth (3) Sulfate | 15.0 | 15.0 | 15.0 |
| Ammonium Lauryl Sulfate | 5.0 | 5.0 | 5.0 |
| Cocoamidopropyl Betaine | 1.5 | 1.5 | 1.5 |
| Sodium Sulfate | 0.8 | 0.8 | 0.8 |
| Polyquaternium 10¹ | 0.0 | 0.025 | 0.05 |
| Dow Corning 1664 Silicone Emulsion | 1.0 | 1.0 | 1.0 |
| Perfume Solution | 0.65 | 0.65 | 0.65 |
| DMDM Hydantoin | 0.2 | 0.2 | 0.2 |
| Color Solution (ppm) | 10 | 10 | 10 |
| Water | qs | qs | qs |

| Component | Example No. | | |
|---|---|---|---|
| (%, by weight, of composition) | XXX | XXXI | XXXII |
| Ammonium Laureth (3) Sulfate | 15.0 | 15.0 | 15.0 |
| Ammonium Lauryl Sulfate | 5.0 | 5.0 | 5.0 |
| Betaine | 1.5 | 1.5 | 1.5 |
| Sodium Sulfate | 0.8 | 0.8 | 0.8 |
| Polyquaternium 10¹ | 0 | 0.025 | 0.05 |
| 60:40 Blend Dimethicone gum/fluid | 1.0 | 1.0 | 1.0 |
| Perfume Solution | 0.65 | 0.65 | 0.65 |
| DMDM Hydantoin | 0.2 | 0.2 | 0.2 |
| Color Solution (ppm) | 10 | 10 | 10 |
| Water | qs | qs | qs |

As described above, the compositions of Examples XXI–XXXII were stability tested at 49° C. Example XXI, which did not contain cationic polymer or any conventional suspending agent, creamed after four weeks. Comparative Examples XXII and XXIII, which are representative of the present invention, remained stable without the need for conventional crystalline suspending agents or polymeric thickening agents. By "creamed" what is meant is that a layer of silicone separated and collected at the top of the product.

Likewise, Example XXIV creamed after four weeks without the aid of cationic polymer or a conventional suspending agent, whereas Comparative Examples XXV and XXVI, which are representative of the present invention, remained stable.

Example XXVII creamed after one week, without the aid of cationic polymer, whereas Comparative Examples XXVIII and XXIX, which are representative of the present invention, remained stable.

Example XXX, which does not contain cationic polymer or any conventional suspending agent, creamed after five weeks, whereas Comparative Examples XXXI and XXXII, which are representative of the present invention, remained stable.

What is claimed is:

1. A conditioning shampoo composition comprising:
   (a) from about 8% to about 40%, by weight, of detersive surfactant, said composition containing at least about 5%, by weight, of anionic detersive surfactant;
   (b) from about 0.05% to about 5%, by weight, of an insoluble silicone conditioning agent said conditioning agent being in the form of dispersed droplets of insoluble silicone having an average particle size of at least 2 microns;
   (c) from about 0.01% to about 1%, by weight, of a stabilizing agent for said silicone conditioning agent, said stabilizing agent being a shampoo soluble cationic polymer;
   (d) from about 50% to about 91.5%, by weight, water;
   wherein said shampoo composition is substantially free of suspending agents selected from the group consisting of crystalline suspending agents, crosslinked acrylic/acrylate polymer suspending agents and anionic, amphoteric, and nonionic polymeric thickening agents.

2. A shampoo composition as in claim 1, wherein said composition comprises at least about 10%, by weight, of said detersive surfactant.

3. A shampoo composition as in claim 2, wherein said cationic polymer has a weight average molecular weight of at least about 200,000 and a charge density of at least about 0.3 milliequivalent/gram.

4. A shampoo composition as in claim 3, wherein said cationic polymer has a weight average molecular weight of from about 400,000 to about 2,000,000 and a charge density of from about 0.6 milliequivalent/gram to about 4 milliequivalent/gram.

5. A shampoo composition as in claim 1, wherein said insoluble silicone conditioning agent has a number average particle size of from 2 microns to about 35 microns.

6. A shampoo composition as in claim 4, wherein said insoluble silicone conditioning agent has a number average particle size of from 2 microns to about 25 microns.

7. A shampoo composition as in claim 1, wherein said insoluble silicone conditioning agent is polydimethylsiloxane.

8. A shampoo composition as in claim 1, wherein said composition contains about 0.3%, by weight, or less of said suspending agents.

9. A shampoo composition as in claim 8, wherein said composition contains about 0.1%, by weight, or less of said suspending agents.

10. A shampoo composition as in claim 9, wherein said composition contains about 0.05%, by weight, or less of said suspending agents.

11. A shampoo composition as in claim 1, wherein said composition comprises:

(a) from about 10% to about 30%, by weight, of said detersive surfactant, said composition containing from about 8% to about 25%, by weight, of said anionic detersive surfactant;

(b) from about 0.1% to about 3%, by weight, of said silicone conditioning agent; and (c) from about 0.02% to about 0.5%, by weight, of said stabilizing agent.

12. A shampoo composition as in claim 11, wherein said insoluble silicone conditioning agent has a number average particle size of from 2 microns to about 50 microns.

13. A shampoo composition as in claim 12, wherein said insoluble silicone conditioning agent has a number average particle size of from 2 microns to about 25 microns.

14. A shampoo composition as in claim 12, wherein said cationic polymer has a weight average molecular weight of at least about 400,000 and a charge density of at least about 0.3 milliequivalent/gram.

15. A shampoo composition as in claim 14, wherein said composition comprises from about 12% to about 25%, by weight, of said detersive surfactant including from about 10% to about 22%, by weight, of said anionic detersive surfactant, said anionic detersive surfactant being selected from the group consisting of alkyl sulfates, alkyl ethoxylated sulfates, and combinations thereof.

16. A shampoo composition as in claim 13, wherein said insoluble silicone conditioning agent is polydimethylsiloxane.

17. A shampoo composition as in claim 16, wherein said insoluble silicone conditioning agent is polydimethylsiloxane.

18. A shampoo composition as in claim 17, wherein said cationic polymer has a weight average molecular weight of from about 800,000 to about 2,000,000 and a charge density of from about 0.6 milliequivalent/gram to about 4 milliequivalent/gram.

19. A shampoo composition as in claim 11, wherein said cationic polymer is selected from the group consisting of polyquaternium-10 and guar hydroxypropyltrimonium chloride and mixtures thereof wherein said cationic polymer has a weight average molecular weight of from about 800,000 to about 2,000,000 and a charge density of from about 0.6 meq/g to about 4 meq/g.

* * * * *